(12) United States Patent
Zheng

(10) Patent No.: US 10,822,373 B2
(45) Date of Patent: Nov. 3, 2020

(54) METHODS FOR SYNTHESIZING PHYCOCYANIN USING A BIOLOGICAL SUBSTANCE

(71) Applicant: Chenghui Zheng, Northhampton, MA (US)

(72) Inventor: Chenghui Zheng, Northhampton, MA (US)

( * ) Notice: Subject to any disclaimer, the term of this patent is extended or adjusted under 35 U.S.C. 154(b) by 0 days.

(21) Appl. No.: 16/717,390

(22) Filed: Dec. 17, 2019

(65) Prior Publication Data

US 2020/0216489 A1    Jul. 9, 2020

Related U.S. Application Data

(60) Provisional application No. 62/790,414, filed on Jan. 9, 2019.

(51) Int. Cl.
| | | |
|---|---|---|
| *C07K 14/405* | (2006.01) | |
| *C07K 1/14* | (2006.01) | |
| *C07K 1/36* | (2006.01) | |
| *C07K 1/34* | (2006.01) | |

(52) U.S. Cl.
CPC ............... *C07K 1/145* (2013.01); *C07K 1/34* (2013.01); *C07K 1/36* (2013.01); *C07K 14/405* (2013.01)

(58) Field of Classification Search
None
See application file for complete search history.

(56) References Cited

U.S. PATENT DOCUMENTS

| | | |
|---|---|---|
| 4,851,339 A | 7/1989 | Hills |
| 8,563,701 B2 | 10/2013 | Ehmann et al. |
| 2015/0239941 A1 | 8/2015 | Pottecher |
| 2017/0136075 A1 | 5/2017 | Choung et al. |

FOREIGN PATENT DOCUMENTS

| | | |
|---|---|---|
| CN | 101891809 A | 11/2010 |
| CN | 103408657 A | 11/2013 |
| CN | 103554250 A | 2/2014 |
| CN | 104292327 A | 1/2015 |
| WO | 2012104091 A1 | 8/2012 |
| WO | 2018033814 | 2/2018 |
| WO | 18172708 A1 | 9/2018 |

OTHER PUBLICATIONS

Jaouen, P. et al, Biotechnol. Tech. 1999 vol. 13 pp. 877-881.*
R Sarada, Manoj G Pillai, G.A Ravishankar, Phycocyanin from Spirulina sp: influence of processing of biomass on phycocyanin yield, analysis of efficacy of extraction methods and stability studies on phycocyanin, article, Nov. 29, 1998 https://www.sciencedirect.com/science/article/pii/S0032959298001538.
Suresh P. Kamble, Rajendra B. Gaikar , Rimal B. Padalia and Keshav D. Shinde, Extraction and purification of Cphycocyanin from dry Spirulina powder and evaluating its antioxidant, anticoagulation and prevention of DNA damage activity, journal, Aug. 30, 2013 http://www.japsonline.com/admin/php/uploads/1013_pdf.pdf.
Fernandes De Medeiros Burkert, Susana Juliano Kalil, Process for Largescale Use https://onlinelibrary.wiley.com/doi/pdf/10.1111/j.1745-4514.2009.00317.x.

* cited by examiner

*Primary Examiner* — Heidi Reese
(74) *Attorney, Agent, or Firm* — Caldwell Intellectual Property Law

(57) ABSTRACT

Methods for synthesizing phycocyanin using a biological substance include first synthesizing the phycocyanin by receiving a source containing phycocyanin, forming a solution by adding the source to water, extracting the phycocyanin from the source containing phycocyanin, such as by lysing cell walls and adding chemical reagents to assist in the extraction process, separating the phycocyanin from the solution by using a filter, processing the solution through a centrifuge, and sterilizing the phycocyanin.

18 Claims, 6 Drawing Sheets

METHODS FOR SYNTHESIZING PHYCOCYANIN USING A BIOLOGICAL SUBSTANCE

CROSS-REFERENCE TO RELATED APPLICATIONS

This application claims the benefit of priority of U.S. Provisional Patent Application Ser. No. 62/790,414, filed on Jan. 9, 2019, and titled "METHODS FOR SYNTHESIZING PHYCOCYANIN USING A POWDERED BIOLOGICAL SUBSTANCE," which is incorporated by reference herein in its entirety.

FIELD OF THE INVENTION

The present invention generally relates to the field of plant chemistry and extraction. In particular, the present invention is directed to methods for synthesizing phycocyanin using a powdered biological substance.

BACKGROUND

Phycocyanin is naturally occurring in nature, existing as both algal and cyanobacterial sources. Phycocyanin has many uses including its natural blue color which has been used as an additive in the food and cosmetic industry. Phycocyanin has been used as a fluorescent reagent for medical research and diagnosis. Phycocyanin has been shown to have antioxidant activity as well as anti-inflammatory activity. It is difficult to extract phycocyanin from the substances in which it is found in nature, resulting in costly and inefficient practices for extraction of phycocyanin. This has hampered its use.

SUMMARY OF THE DISCLOSURE

In an aspect, a method for synthesizing phycocyanin using a biological substance includes receiving a biological substance containing phycocyanin. The method includes adding the biological substance to water to form a solution. The method includes extracting the phycocyanin from the biological substance in the solution. The method includes separating the phycocyanin from the solution. The method includes sterilizing the phycocyanin, wherein sterilizing the phycocyanin further comprises sterilizing the separated phycocyanin using a ceramic membrane.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to methods for synthesizing phycocyanin using a powdered biological substance. In an embodiment, the disclosed method provides for the synthesis of phycocyanin using methods to ensure purity and safety. In an embodiment, disclosed methods provide for safety by sterilizing separated phycocyanin to ensure removal of potentially harmful pathogens that may occur naturally in nature. Phycocyanin is often found in algal and bacterial sources in nature that can sometimes exist in nature together with harmful pathogens such as for example, e-coli. In an embodiment, sterilization methods such as ceramic membrane sterilizers and application of heat help ensure destruction of harmful pathogens while ensuring purity and integrity of extracted phycocyanin. Rigor in phycocyanin synthesis ensures adequate extraction and purification to produce a final product of phycocyanin existing as a powdered substance.

Figure 1:
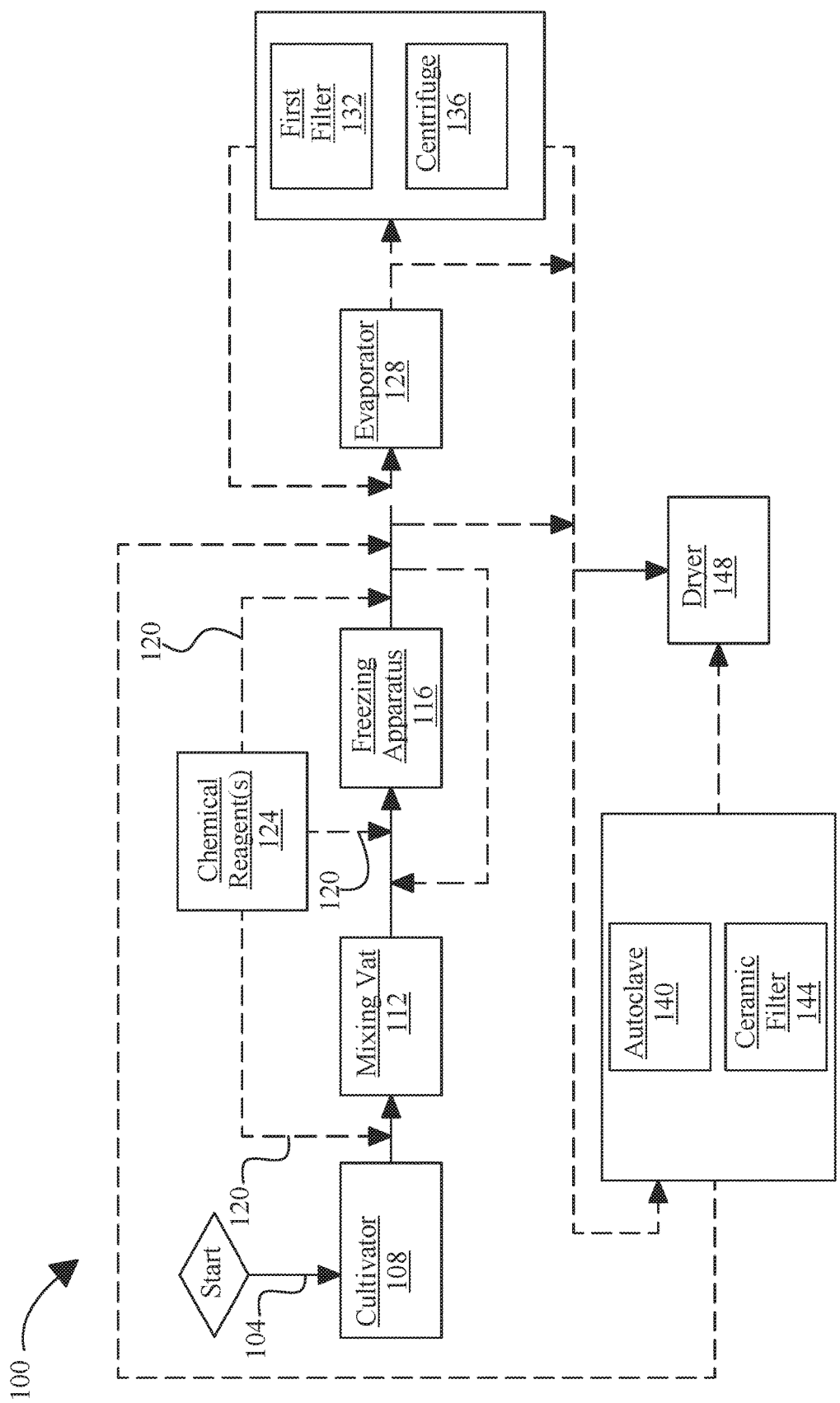
FIG. 1 is a process flow diagram illustrating exemplary embodiments of methods and stages for synthesizing phycocyanin using a powdered biological substance.

Referring now to FIG. 1, a block diagram illustrates a process flow 100 for synthesizing phycocyanin using a biological substance. A biological substance containing is received 104. Biological substance may include one or more biological organisms and/or parts thereof containing phycocyanin. For instance, and without limitation, biological substance may include a culture of one or more living phycocyanin-bearing organisms, such as without limitation an algal source of phycocyanin. An algal source as used herein may include any organism, population of organisms, and/or colony of organisms referred to colloquially or otherwise as algae, including without limitation photosynthetic single-celled organisms, such as eukaryotic photosynthetic organisms and/or prokaryotic single-celled organisms such as cyanobacteria. Photosynthesis is a process used by both plants and organisms to convert light energy into chemical energy, which may be later released to fuel the organisms' activities. Organelles that conduct photosynthesis such as chloroplasts may capture energy from sunlight, convert, and store it as adenosine triphosphate (ATP) and nicotinamide adenine dinucleotide phosphate (NADPH). Eukaryotes are organisms whose cells have a nucleus enclosed within membranes. Eukaryotic cells may also contain other membrane-bound organelles such as mitochondria, and Golgi apparatus. Eukaryotic cells may contain chloroplasts which may be organelles that conduct photosynthesis. Prokaryotic organisms are single-celled or colonial organisms having cells that lack membrane-bound nucleuses and other membrane-bound organelles such as mitochondria, including bacteria, archaea, and the like. Cyanobacteria may include a phylum of bacteria that may obtain their own energy through photosynthesis. Intracellular water-soluble components of prokaryotes may be located together in the cytoplasm enclosed by a cell membrane rather than in separate cellular compartments. Cyanobacteria may exist as large colonies whereby two or more cyanobacteria may live in close association with or be connected to one another. Phycocyanin is a biologically active nutrient compound that belongs to the phycobiliprotein family. Phycocyanin may be obtained from algal sources such as *Chlorella* sp., *Enteromorpha* sp., and *Nannochloropsis* sp. Phycocyanin may be obtained from different species of cyanobacteria such as *Aphanizomenon* sp., *Spirulina* sp., *Phormidium* sp., *Lyngbya* sp., *Synechocystis* sp., and *Synechococcus* sp. Phycocyanin may be comprised of alpha ($\alpha$) and beta ($\beta$) subunits. $\alpha$ and $\beta$ subunits of phycocyanin may form a stable heterodimeric monomer $\alpha\beta$ which may then polymerize into a multimer $\alpha\beta n$ whereby n may be a number from 1-8. For example, $\alpha\beta 3$ exists as three subunits comprised of $\alpha$ and $\beta$. It may exist as $2\alpha$ and $1\beta$ or $1\alpha$ and $2\beta$. $\alpha$ and $\beta$ subunits may be composed of amino acid residues and may contain anywhere from 160-180 amino acid residues. Amino acid residues may include the part of an amino acid that is unique to each of the 20 different amino acids. An amino acid may include an amine group (H2N), a carboxylic acid group (C(=O)OH), and the residue. Amino acid residues may be hydrophilic in that they are water soluble while some amino acid residues may be hydrophobic, in that they are not water soluble. Amino acid residues may be polarized and carry a charge, whereas some amino acid residues may be nonpolar meaning they do not carry a charge. Amino acid residues may align themselves based on hydrophilicity and hydrophobicity and/or charge and form complexes with unique shapes such as an alpha-helix or beta pleated sheets. Amino acid residues may also link together and form disulfide bridges such as when two cysteine residues bond together. Biological source may include cultures and/or portions of any alternative or additional phycocyanin-bearing organisms.

Figure 2:
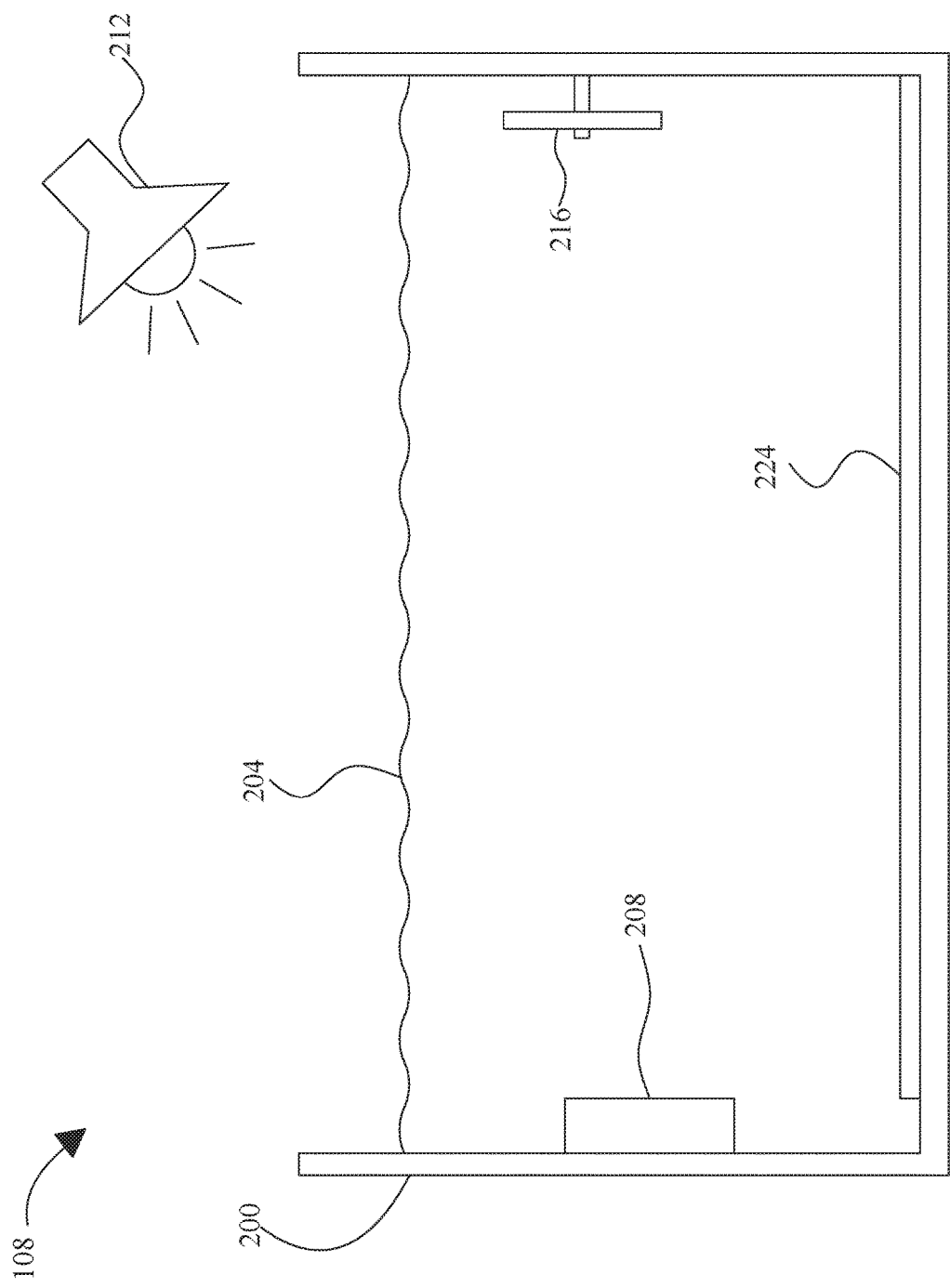
FIG. 2 is a schematic diagram illustrating an exemplary embodiment of a cultivator.
Figure 3:
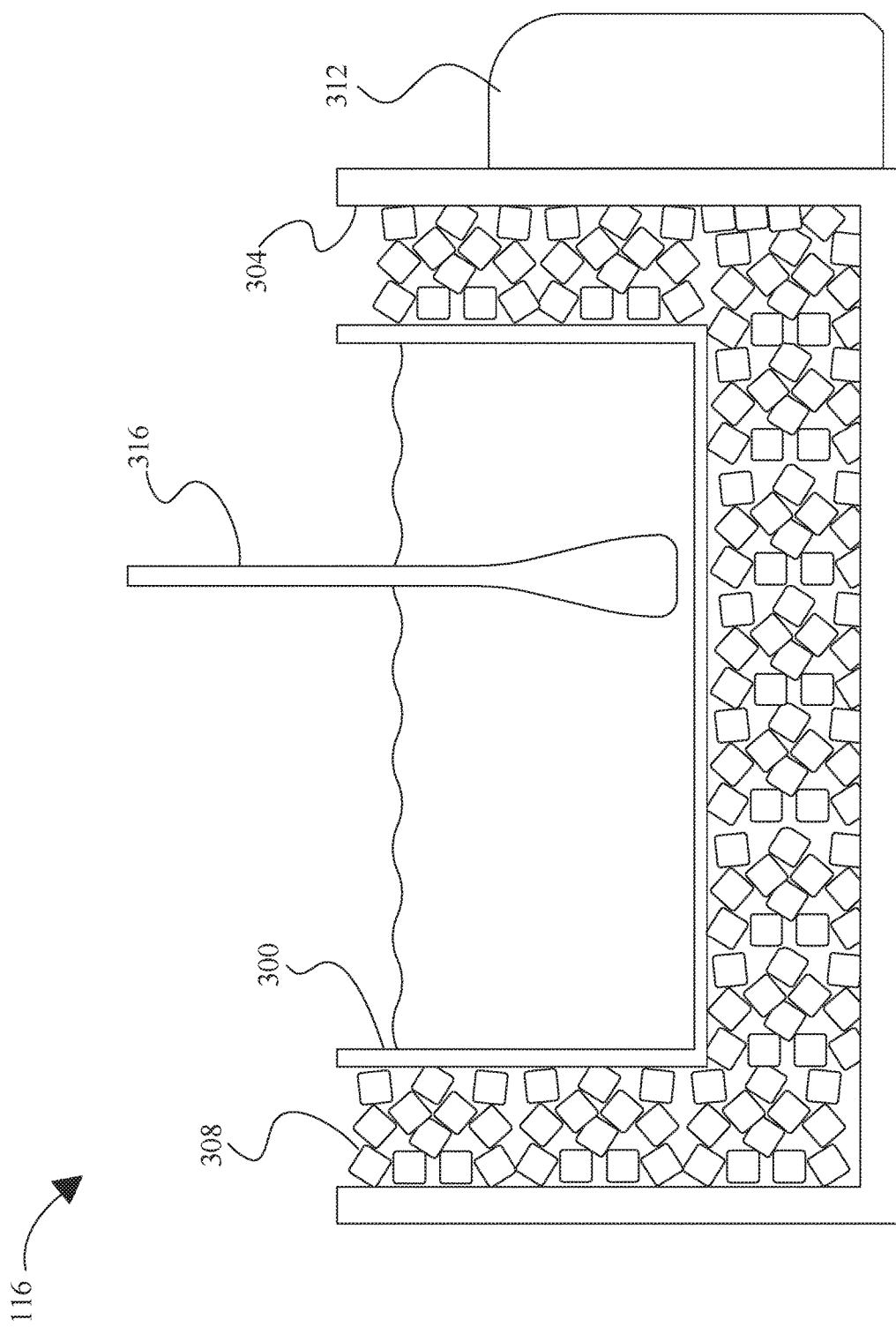
FIG. 3 is a schematic diagram illustrating an exemplary embodiment of a freezing apparatus.

Still referring to FIG. 1, receipt of biological substance 104 may include culturing and/or cultivation of an organism making up or producing biological substance in a cultivator 108. Cultivation and/or culturing of a biological source may be accomplished by any process wherein the biological source is provided nutrients and/or other conditions necessary for it to increase in biomass through growth, cellular division, propagation, or the like. For instance, and without limitation, an algal source may be cultivated in a liquid suspension exposed to a light source permitting photosynthesis. FIG. 2 illustrates an exemplary embodiment of a cultivator 108 that may be used for cultivation of algal sources as described in this disclosure. Cultivator 108 may include a container 200, within which a liquid suspension 204 of biological source may be contained. Container 200 may be constructed of any suitable material for use in containing liquids such as aqueous suspensions and/or solutions. Container 200 may include an open container 200 such as a pond, tub, vat, or the like. Container 200 may include a photobioreactor, defined herein as a closed or substantially closed container 200 that permits light from a light source 212 as described below to illuminate its contents; for instance, and without limitation, a photobioreactor may have transparent or translucent walls, and/or may have an integrated light source 212 that illuminates liquid suspension 204.

Still referring to FIG. 2, liquid suspension 204 may include biological source, water, and/or one or more nutrients conducive to cultivation of biological source, including without limitation nutrients containing nitrogen, phosphorus, potassium, iron, silica, sodium bicarbonate, magnesium sulfate, potassium nitrate, citric acid, salt, urea, calcium chloride, iron sulfate, ammonium sulfate, or the like. Persons skilled in the art, upon reviewing the entirety of this disclosure, will be aware of various alternative or additional nutrients that may be included. Nutrients and/or chemical components of liquid suspension 204 may be provided in concentrations typical in a natural environment of biological source, such as concentrations of marine salts commensurate with a natural environment of a marine organism, concentrations of salts and/or other chemical found in natural environments of extremophile biological sources, or the like. Liquid suspension 204 may include one or more sources of food for biological source, such as without limitation any organic or inorganic substance used by biological source as a source of energy by means of digestion, chemosynthesis, or the like.

Continuing to refer to FIG. 2, cultivator 108 may include a temperature regulator 208. Temperature regulator 208 may include any heat source, heating element, heat sink, cooling device, or other device and/or component usable to modify a temperature of liquid suspension 204, and/or a control circuit suitable for detection and/or regulation of such temperature, for instance and without limitation using sensor feedback. Temperature regulator 208 may include, without limitation, a resistive heating element, a heating element that uses combustion, or the like. Temperature regulator 208 may sense temperature electronically and adjust temperature automatically using a control circuit. Control circuit may include, without limitation, any analog and/or digital feedback circuit, including without limitation a circuit that compares electrical parameters output from a temperature sensor to a reference parameter, such as without limitation a reference voltage, using for instance a comparator and/or switching diode; alternatively or additionally, control circuit may regulate temperature using one or more logic circuits, which may include without limitation a microcontroller, microprocessor, and/or any computing device and/or component thereof as described in this disclosure. Control circuit may be integrated in temperature regulator 208 and/or may communicate therewith via any wired and/or wireless communication means or protocol. Temperature regulator 208 may maintain liquid suspension 204 at a temperature and/or temperature range suitable for growth of biological source; for instance, and without limitation, temperature regulator 208 may maintain *spirulina* in a liquid suspension 204 at about 35 degrees Celsius (95 degrees Fahrenheit), while *chlorella* may be maintained at a temperature between approximately 26 degrees Celsius (78.8 degrees Fahrenheit) and 30 degrees Celsius (86 degrees Fahrenheit). Temperature may alternatively or additionally be maintained by ambient temperature around cultivator 108, including without limitation a temperature of a room and/or outdoor environment where cultivator 108 is located.

Still referring to FIG. 2, cultivator 108 may include a light source 212 that illuminates liquid suspension 204. Light source 212 may include an electrical light and/or bank of lights. Light source 212 may include one or more light-emitting diodes (LEDs), fluorescent bulbs, incandescent bulbs, or the like; light source 212 may include "grow lights" having an emission spectrum optimal for growth of and/or photosynthesis by biological source. Light source 212 may be continuously emitting and/or may be on a timer and/or schedule whereby light is emitted for a certain first period of time, followed by a second period of time in which light is not emitted; such on and off periods for light source 212 may, without limitation, imitate "day" and "night" of a diurnal cycle. Day/night cycles may be set and/or regulated using a light timer. Alternatively, a control circuit, which may contain any elements suitable for use as a control circuit in temperature regulator 208, may switch light source on or off according to one or more diurnal cycles that may, e.g., be programmed into memory of control circuit. Control circuit may be combined with and/or in communication with any other control circuit as described in this disclosure. Alternatively or additionally, liquid suspension 204 may be illuminated by natural light such as sunlight; any possible source of light may be used exclusively or may be supplemented and/or combined with any other possible source of light.

With continued reference to FIG. 2, cultivator 108 may include an agitator 218. Agitator 218 may include an impeller, propeller, stirring arm, or other device that causes turbulence and/or flow of liquid suspension 204. Agitator 218 may impel liquid suspension 204 in a circular or "raceway" path through container 200; alternatively or additionally, liquid suspension 204 may be impelled by agitator 218 in thin layers over inclined surfaces, which may be textured to introduce a desired degree of turbulence. Agitation may be performed on a schedule; for instance, liquid suspension 204 may be stirred and/or forced over surfaces while illuminated and stored in vats and/or container 200 when not illuminated. Agitation may be performed continually and/or according to a duty cycle, which may be controlled manually and/or automatically using a control circuit, which may contain any elements suitable for use as a control circuit in temperature regulator 208; control circuit may be combined with any control circuit as described in this disclosure.

Still referring to FIG. 2, cultivator 108 may include an aerator 224. Aerator 224 may be any device that introduces bubbles of gas into liquid suspension 204, for instance and without limitation by agitation and/or splashing or by release of bubbles into liquid suspension 204 from one or more lines or tubes of air; air may be forced through lines or tubes by a fan, air-pump, impeller, or the like. Gas may include any gas beneficial to and/or aiding in cultivation of biological source, including without limitation oxygen and/or carbon dioxide. Aeration with gas may, for instance and without limitation, provide biological source with chemicals needed for photosynthesis and/or cellular respiration. Aeration may be performed continuously, and/or may be performed on a duty cycle, for instance using a control circuit, which may contain any elements suitable for use as a control circuit in temperature regulator 208; control circuit may be combined with any control circuit as described in this disclosure. Alternatively or additionally, control circuit may measure one or more chemical indicators using, e.g., an electrochemical sensor, for instance to detect concentrations of dissolved carbon dioxide and/or oxygen in liquid suspension 204, and start, stop, and/or modify rate of aeration in response.

In an embodiment, and still referring to FIG. 2, liquid suspension 204 may be tested for concentration of biological source, where concentration may include a number of organisms per unit of volume, a proportion in volume of organisms, and/or a proportion per unit mass of biological source. As a non-limiting and illustrative example, concentration may be determined by a process of cell-counting, wherein a sample of liquid suspension 204 having a given volume may be viewed by a person and/or automated device that counts a number of cells, such as cells of a single-celled organism such as an algal source as described above. A person counting cells may do so using a microscope; automated cell counters may operate using optical detection methods. A number of cells per sample may be multiplied by a number of samples in liquid suspension 204 as a whole to determine an overall quantity of cells; alternatively or additionally, a volume and/or mass of biological substance represented by an enumeration of cells in sample may be computed and compared to a volume and/or mass of sample to determine a concentration as a ratio and/or fraction.

Alternatively or additionally, and continuing to refer to FIG. 2, concentration of biological source in liquid suspension 204 may be computed via gravimetric methods; gravimetric methods include any method whereby a density and/or weight of a sample of liquid solution is computed. For instance, and without limitation, specific gravity of solution may be computed using a hydrometer, which may determine specific gravity and/or density using buoyancy; hydrometer and/or measurements derived therefrom may be calibrated to match density and/or specific gravity readings to concentrations of biological source. As another non-limiting example, gravimetric methods may include weighing a sample of solution. Weight may be calibrated to concentration of biological source; alternatively or additionally, biological source may be filtered from sample using any filter and/or centrifuge as described in further detail below, which may be weighed a second time; a difference in weight pre- and post-filtering may be a wet weight of biological source. As another non-limiting example, a sample may be evaporated, which may be accomplished using any methods described below including without limitation heating and/or nozzle drying, and a resulting residue may be weighed to determine a dry weight of biological source.

Still referring to FIG. 2, concentration may alternatively or additionally be determined using chemical tests, such as extraction and measurement of a signature chemical from a sample. For instance, and without limitation, algae biomass in water may be measured by measurement of chlorophyll-a in the sample, for instance, and without limitation using a fluorometer and/or a spectrometer. Only photosynthetic organisms contain chlorophyll-a; as a result, chlorophyll-a measurement may measure only concentrations of algae in liquid suspension 204. Concentrations may be measured, alternatively or additionally, using spectrophotometric measurements or the like of, e.g., color according to the Lovibond scale, or the like. Determination of concentration may be performed using any computing device as described herein, for instance using optical sensors and/or cameras, for instance and without limitation in combination with light sources to detect color and/or spectrophotometric measurements, using electrochemical sensors for measurement of signature chemicals, or the like.

Continuing to refer to FIG. 2, measurements of concentration may be used to determine when to terminate cultivation and proceed to subsequent steps; for instance, when concentration arrives at a threshold number, extraction method may proceed to subsequent method steps such as extraction steps as described in further detail below. For instance, and without limitation, cultivated biological source may be moved to a subsequent step in process 100 when a mass ratio of the dry and/or wet mass of biological source to mass of water is be between about 1:15 and about 1:8. For example, where 50 kilograms of biological source, dry mass or wet mass, is mixed with 750 kilograms of water, a mass ratio of 1:15 may be achieved while 50 kilograms, dry mass or wet mass, of biological source in 400 kilograms of water may result in a mass ratio of 1:8. Alternatively or additionally, a concentration determined by any process as described above may be used to determine what quantity and/or concentration of a chemical addition is to be made, for instance as described in further detail below. Determination may be performed, without limitation, using any control circuit and/or computing device as described herein; for instance, and without limitation, a control circuit and/or computing device may detect when concentration of biological substance exceeds a threshold number stored in memory, which detection may activate a conveyance to a subsequent station and/or step in process 100 and/or alert a user to convey to a subsequent station and/or step in process 100. Alternatively or additionally, a control circuit may automatically set amounts of chemical reagents to be dispensed, either manually or automatically, according to detected concentrations.

Referring again to FIG. 1, biological substance may alternatively or additionally be received as a powder, either in dry form, or combined with a liquid in a, slurry, suspension, solution, or the like. Powdered form may include, without limitation, fine dry particles of biological substance that may be produced by evaporation, grinding, crushing, and/or disintegration from a solid form of biological substance; grinding, crushing, and/or disintegration may be performed as part of process 100 and/or may have been performed by a third party providing biological substance. In a non-limiting example, biological substance may be powdered and/or dried after cultivation, as described above, and a resulting powder may be used in subsequent steps of process 100. Powdered may include very fine particles that may flow freely when shaken or tilted. A powdered biological substance may include an algal or cyanobacterial source that exists in powdered form and/or is converted to a powdered form; powdered biological substance may include an algal flour of any algae, including without limitation *spirulina*. Powdered biological substance may include cell membranes and/or cell walls containing phycocyanin.

Still referring to FIG. 1, biological substance may be combined with water to form a solution, for instance in a mixing vat 112, which may include any open and/or closed container; combination with water may be accomplished by culturing in an aqueous suspension as described above and/or by addition of powder, slurry, paste, a cake or block of material, any dry form of biological substance, and/or aqueous suspension to some volume of water. A solution may include a homogenous mixture composed of two or more substances. When a powdered biological substance is added to water it forms an aqueous solution whereby the solvent is water. A solvent may include a substance that a solute is dissolved in. A solute may include a substance that is dissolved into a solvent. For example, when a powdered biological substance is added to water, the powdered biological substance may be the solute, dissolved in water, which may be the solvent. As used herein, a solution may also include a suspension, which may include a heterogenous mixture in which particles such as solute particles, powdered biological substance, or the like may settle out of a solvent, either because of saturation or because the particles include particles that are not insoluble or not fully soluble in the solvent. Settling out of solution and/or precipitation may occur sometime after their introduction. In an embodiment, if the solute particles that do not dissolve in the solvent are too small to settle, they may form a colloid. Solution containing powered biological substance may include a solution, a suspension, and/or a colloid, or any combination thereof; for the sake of simplicity, all such mixtures of powdered biological substance with water are referred to herein as "solutions." In an embodiment, a powdered biological substance may be added to water to form a solution at certain ratios of a powdered biological substance to water. In an embodiment, the mass ratio between a powdered biological substance and water may be between about 1:15 and 1:8; mass ratio may alternatively or additionally fall in other ranges, such as be between about 1:50 and about 1:2, between about 1:30 and about 1:4, or the like. The mass ratio may be calculated by taking the mass of each compound in equal units of measurement and dividing the larger value by the smaller value. For example, and without limitation, 50 kilograms of a powdered biological substance may be added to 750 kilograms of water, thereby achieving a mass ratio of 1:15. In yet another non-limiting example, 50 kilograms of a powdered biological substance may be added to 400 kilograms of water, thereby achieving a mass ratio of 1:8.

Still referring to FIG. 1, process 100 may include one or more steps to extract phycocyanin from biological substance. Extracting may include removing and/or taking out phycocyanin from cell walls or other components of biological substance in solution, permitting the phycocyanin to be isolated as described in further detail below. Extraction may be accomplished, without limitation, by fracturing cell walls or cell membranes of biological substance, for instance by thawing and freezing the solution. Extracting may be performed by freezing and thawing the solution at least once. Freezing and thawing may work as a mechanical form of lysis. Lysis may include breaking open cell membranes of a powdered biological substance to further purify and extract their contents. In an embodiment, phycocyanin may be found in cell membranes, and mechanical lysis through freezing and thawing may be performed in order to extract phycocyanin that may be located in the cell membrane. Freezing may be performed, without limitation, using a freezing apparatus 116.

Referring now to FIG. 3, an exemplary embodiment of a freezing apparatus 116 is illustrated. Freezing apparatus 116 may include an interior chamber 300 in which solution may be contained. Interior chamber 300 may be mixing vat 112 or may be a different container. Freezing apparatus 116 may include one or more elements that extract heat from solution to cause solution to freeze. Freezing may be performed, as a non-limiting example, by adding interior chamber 300 to an outer chamber 304 or receptacle containing ice 308 such as water ice, carbon dioxide ice, or the like, a cryogenic or refrigerant fluid such as liquid nitrogen, liquid freon, or the like, and/or another cold material suitable for causing an aqueous solution to freeze, whereby the interior chamber 300 is surrounded by ice 308 or other cooling agent but the solution has no direct contact with the ice 308. In an embodiment, the container of ice 308 and/or other cooling agent may be kept at a target temperature and/or temperature range, including without limitation a temperature below about 0 degrees Celsius, a temperature below about −10 degrees Celsius, a temperature between about −10 and about −30 Celsius, and/or a temperature within some tolerance number of degrees, such as without limitation 1 degree, 5 degrees, or the like about a target temperature, which may include without limitation any temperature described above and/or any temperature falling within ranges as described above. Ice 308 may be continuously added to the container to maintain adequate temperature. Freezing may also be performed by placing the solution in a freezer or in thermal communication with a cooling mechanism 312. In an embodiment, the freezer may be kept at a target temperature and/or temperature range, including without limitation a temperature below about 0 degrees Celsius, a temperature below about −10 degrees Celsius, a temperature between about −10 and about −30 Celsius, and/or a temperature within some tolerance number of degrees, such as without limitation 1 degree, 5 degrees, or the like about a target temperature, which may include without limitation any temperature described above and/or any temperature falling within ranges as described above. Thawing the solution may include permitting the frozen solution to be allowed to stand at an ambient temperature that is above the freezing temperature of water and/or of the solution, so that the solution becomes free from ice 308. In an embodiment, during the freezing and thawing process the solution may be continuously and/or repeatedly stirred by a stirring mechanism 316. Stirring may be performed manually and/or stirring may be performed automatically such as for example with the use of magnetic stirrer. A magnetic stirrer may include a device that employs a rotating magnetic field to cause a stir bar immersed in the solution to spin, thus stirring it. Stirring, in an embodiment, may prevent the solution from freezing solid. Thawing may be performed, without limitation, using a heating element (not shown), which may be incorporated in freezing device and/or in a separate unit or location. Thawing and freezing may be repeated two or more times. In an embodiment, freezing and thawing may occur 2-8 times. Each of temperature regulation, stirring, activation of cooling and/or heating apparatuses, and/or any other actions performed using freezing apparatus 116 may be performed manually by a user, and/or automatically using a control circuit, which may contain any elements suitable for use as a control circuit in temperature regulator 208; control circuit may be combined with any control circuit as described in this disclosure, and may be coupled to any mechanical devices and/or sensors suitable for performance of above-described steps, including without limitation cooling mechanism 312, stirring mechanism 316, a temperature sensor, a heating element, a conveyance mechanism to convey frozen solution to a heating apparatus, a conveyance mechanism to convey solution into freezing apparatus 116, or the like.

Referring again to FIG. 1, extraction may include introduction 120 of one or more chemical reagents 124 into solution. One or more chemical reagents 124 may include, without limitation, at least a salt. A salt may include an ionic compound that may be formed by the neutralization reaction of an acid and a base. Salts may include cations and anions so that the product is electrically neutral or doesn't have a net charge. For example, one or more chemical reagents 124 may include calcium chloride, potassium chloride, copper sulfate, sodium bicarbonate, magnesium sulfate. One or more chemical reagents 124 may include a chloride-containing compound, such as without limitation sodium hypochlorite. One or more chemical reagents 124 may include sodium bicarbonate, citric acid and/or tartaric acid. One or more chemical reagents 124 may include an acid. An acid may include a substance with a pH of less than 7 and which may donate protons and react with metals such as calcium for example to form salts; acids may include, as a non-limiting example, tartaric acid, acetic acid, and/or oxalic acid. One or more chemical reagents 124 may include disodium hydrogen phosphate. One or more chemical reagents 124 may include sodium nitrate.

With continued reference to FIG. 1, in an embodiment one or more chemical reagents 124 may include a lysate. A lysate, as used in this disclosure, is a chemical reagent and/or mixture thereof derived by rupturing, or "lysis," of cells. Lysates may function to disrupt cell membranes and aid in extracting phycocyanin from a powdered biological substance. Lysates may be included in a buffered solution containing a salt and a base. Choice of lysate to be added may depend on desired pH that may need to be achieved. Non-limiting examples of lysates that may be added to solution include, without limitation and listed from lowest pH (most acidic) to highest pH (most basic), citric acid-sodium hydroxide (pH range 2.2-6.5), sodium citrate-citric acid (pH range 3.0-6.2), sodium acetate-acetic acid (pH range 3.6-5.6), cacodylic acid sodium salt-hydrochloric acid (pH range 5.0-7.4), 2-ethanesulfonic acid-sodium hydroxide (pH range 5.6-6.8), sodium dihydrogen phosphate-disodium hydrogen phosphate (pH range 5.8-8.0), imidazole-hydrochloric acid (pH range 6.2-7.8), 3-morpholinopropane-1-sulfonic acid-potassium hydroxide (pH range 6.6-7.8), Tri-ethanolamine hydrochloride-sodium hydroxide (pH range 6.8-8.8), 2-amino-2-hydroxymethyl-propane-1,3-diol-hydrochloric acid (pH range 7.0-9.0), 4(2-hydroxyethyl)-1-piperazineethanesulfonic acid-sodium hydroxide (pH range 7.2-8.2), Tricine-sodium hydroxide (pH range 7.6-8.6), sodium tetraborate-boric acid (pH range 7.6-9.2), bicine-sodium hydroxide (pH range 7.7-8.9), and/or Glycine-sodium hydroxide (pH range 8.6-10.6). Lysate may be added in increasing quantity as pH of solution is adjusted to a desired pH. In an embodiment, lysate may be used at any suitable concentrations, including without limitation concentrations ranging from about 20 millimoles to about 50 millimoles. Alternatively or additionally, measurement of concentration a lysate produced by fracture of cells and/or cell walls of biological substance may be used to determine a proportion of cells and/or cell walls that have been fractured; this may in turn be used to determine, without limitation, whether to perform an additional freeze-thaw cycle. For instance, and without limitation, a concentration of a given lysate in solution may be measured using without limitation electrochemical, chemical, and/or spectrographic means, and compared to a threshold number; where lysate concentration is below the threshold number, an additional freeze-thaw cycle may be performed, and/or an additional chemical introduction 120 may be performed. Such lysate measurement feedback may be performed between or during any step and/or steps of process 100. Lysate concentration measurement and/or feedback, as well as determination to perform or not to perform additional freeze-thaw cycles and/or chemical introductions may be performed by a user and/or using a control circuit, which may contain any elements suitable for use as a control circuit in temperature regulator 208; control circuit may be combined with any control circuit as described in this disclosure.

Still referring to FIG. 1, one or more chemical reagents 124 may be added a single time and/or in two, three, or more stages and/or additions. Additions 120 of chemical reagents 124 may be performed prior to after, or between freeze-thaw cycles, if any. In an embodiment, sequentially and/or simultaneously added reagents may react with one another to remove at least one of added reagent from solution. For example, and without limitation, one reagent may have an acidic PH while another has an alkaline PH; as a result, alkaline and acid reagents may react, converting the combined chemicals to a solid precipitate and/or gas, which may then be removed by ventilation, centrifuge, filtration, or the like, for instance as described in further detail below. In an embodiment, chemical reagents 124 may be added in relative quantities sufficient to cause one or all of the chemical agents to be removed entirely from solution, and/or to be removed to a concentration below some desired level. Removal of one or more chemical reagents 124 may be tested; for instance, a sample of solution may be subjected to one or more dye-based tests, titration procedures, or the like to detect whether a given chemical is present and/or whether a given chemical has been removed down to some threshold concentration as determined, without limitation, by levels conducive to health and/or food quality and/or chemical content regulations. Persons skilled in the art, upon reviewing the entirety of this disclosure, will be aware of various ways in which reagents may be combined to remove one or all such reagents to a desired concentration or tolerance. Introduction 120 of chemical reagents, including coordination of introductions 120 with alternative or additional steps, calculations of amounts to introduce, or the like, may be directed and/or performed by a control circuit, which may contain any elements suitable for use as a control circuit in temperature regulator 208; control circuit may be combined with any control circuit as described in this disclosure.

In an embodiment, and with continued reference to FIG. 1, introduction of chemical reagents 124 may depend on concentration of biological substance and/or source, for instance as determined above. Each subsequent chemical reagent may be introduced in an amount that depends on concentration of previous chemical and/or tests such as PH tests, titration of samples, or the like. For instance, and as a non-limiting illustration, one chemical agent may be added so that the ratio of wet and/or dry mass of biological substance to mass of chemical agent is 1:0.7, another chemical agent may be added so that the ratio of wet and/or dry mass of biological substance to mass of chemical agent is between 5:3 and 15:8, yet another chemical agent may be added so that the ratio of wet and/or dry mass of biological substance to mass of chemical agent is between 1:1200 and 1:1250 and still another chemical agent may be added so that the ratio of wet and/or dry mass of biological substance to mass of chemical agent is between 1:2500 and 1:600. Ratios, quantities, and/or concentrations of chemical agents added to solution may be computed in alternative or additional ways. For instance, in an embodiment, 5-40 ml of a chemical reagent may be added to the solution for every 50 kg of biological substance by dry and/or wet mass that may be in solution. As a further example, where 100 kg of biological substance by dry and/or wet mass is included in solution, 10-80 ml of a chemical reagent may be added to the solution. In an embodiment, a concentration of one or more chemical reagents in solution, and or another chemical parameter such as pH level or the like, may be measured during and/or after any step, including without limitation during or after any addition, stirring, and/or resting phase as described in this disclosure. A subsequent and/or additional chemical introduction 120 may be performed as a function of a detected concentration of a given chemical reagent; for instance, and without limitation, where a pH level is higher, or lower, than a threshold and/or tolerance about a desired level, which may, e.g., be neutral pH, an amount of a chemical reagent 124 tending to neutralize the pH and/or change it to a desired level through chemical reaction or the like may be calculated, and the calculated amount may be added. As a further non-limiting example, where a concentration of a specific reagent is detected, an amount of another reagent suitable to reduce and/or negate such concentration may be calculated, and the calculated amount may be added to solution. Detection of chemical parameters and resulting calculation and performance of chemical additions may be performed iteratively until a desired chemical balance, or tolerance about a desired chemical parameter, is achieved. Each of the above detection, calculation, and/or addition steps may be performed manually; alternatively or additionally, each step may be performed using a control circuit, which may contain any elements suitable for use as a control circuit in temperature regulator 208; control circuit may be combined with any control circuit as described in this disclosure.

With continued reference to FIG. 1, process 100 may include concentrating solution; concentrating the solution may include evaporating some of the solvent in an evaporator 128 to make the solution more concentrated. Evaporating may include the process by which water transforms form liquid to gas. Evaporation may occur when heat is applied; for instance, evaporator 128 may include a heat source to raise the temperature of the solution and accelerate evaporation. Evaporation may be performed by immersing the solution in a container such as a beaker, in a hot water bath and gently heating the solution so that some of the water may evaporate. Concentration of a solution may be reflected as the abundance of a constituent found in a solution divided by the total volume of a solution. A constituent may be an ingredient found in a solution, for example a concentration may include the amount of constituent phycocyanin found in solution or water. Concentration of a solution may be expressed as mass concentration, molar concentration, number concentration, and/or volume concentration. Mass concentration may be defined as the mass of a constituent dived by the volume of the solution. For example, the mass concentration may be the mass of phycocyanin divided by the volume of the water. Molar concentration may be defined as the amount of a constituent in moles divided by the volume of the solution. Number concentration may be defined as the number of entities of a constituent divided by the volume of the solution. Volume concentration may be defined as the volume of a constituent divided by the volume of the mixture. Concentrating may include adding more phycocyanin and/or reducing the amount of solution that phycocyanin may be dissolved in. In an embodiment, phycocyanin may be concentrated to a goal molecular weight and/or a tolerance about a goal molecular weight, such as without limitation a molecular weight ranging from about 3000 Daltons to about 5000 Daltons. Detection of concentration may be used via any suitable detection process as described above, and may be performed using a control circuit, which may contain any elements suitable for use as a control circuit in temperature regulator 208; control circuit may be combined with any control circuit as described in this disclosure.

With continued reference to FIG. 1, process 100 may include separating phycocyanin from solution. Separating phycocyanin may include filtering solution through a first filter 132 to form a filtrate. Filtering may include passing the solution through a device and/or machine to remove unwanted material that may exist in the solution. A device used in the filtering process may include a filter. A filter may include a porous device for removing impurities and/or solid particles from the solution as the solution passes through the filter. Impurities and/or solid particles may be separated as a means to purify the solution and eliminate undesirable components. A filtrate may include a solution that has passed through a filter. Larger particles and/or accumulated solids may be captured by a first filter 132 while tinier particles as well as liquid solution may pass through, thereby producing a filtrate. In an embodiment, at least a first filter 132 is utilized. In an embodiment, multiple filters may be used. At least a first filter 132 may include a belt filter which may include an industrial machine which contains a pair of filtering clothes and belts through a system of rollers. The solution may be initially fed through a feed hopper which may be sandwiched between two filter clothes. Phycocyanin filtrate may be initially separated from precipitates by gravity followed by squeezing the cloth through the rollers. Remaining solids not containing phycocyanin may be discarded whereby extracted phycocyanin solution may be collected, for example in a container. In an embodiment at least a first filter 132 may include a filter press which may be used to separate the phycocyanin from the solution. A filter press may include a plate and frame filter press, an automatic filter press, and/or a recessed plate filter press. A plate and frame filter press may consist of plates and frames assembled alternatively with the support of a pair of rails. A solution may be passed into the plates and frames with individual separating chambers. For each individual separating chamber there may be one hollow filter frame separated from two filter plates by filter cloths. The solution may flow through a port in each individual frame whereby accumulated solids, which may be later discarded, accumulate in each hollow frame. As more solids accumulate and grow thicker, the filter resistance may increase as well. Eventually when the separating chamber is full, the filtration process is stopped as the optimum pressure difference is reached. Remaining liquid may pass through filter cloth and may be collected through collection pipes stored in the filter tank. Suspended solid accumulation may occur at the hollow plate frame and may be separated at the filter plates by pulling the plate and frame filter press apart.

Still referring to FIG. 1, at least a first filter 132 may alternatively or additionally include an automatic filter press. An automatic filter press may be very similar to a plate and frame filter press except the entire process may be fully automated. An automatic filter press may consist of larger plate and frame filter presses with mechanical plate shifts. Plate shifter may move plates and allow rapid discharge of suspended solids in between the plates. At least a first filter 132 may include a recessed plate filter press. A recessed plate filter press may include plates that join together to form a chamber to pressurize the solution and squeeze solids out through a filter cloth lining located in a chamber. A recessed plate filter press may be comprised of 10 to 100 plates adjacent to one another, depending on filtration capacity requirements. At least a first filter 132 may include a bag filter system. A bag filter system may include at least a bag filter placed inside of a bag filter housing for the purpose of purification by removing accumulated solids from the solution. In an embodiment, a bag filter system may be composed of stainless steel and may carry an approval seal by the American Society of Mechanical Engineers (ASME). A bag filter system may include a circular opening where a solution is initially poured and includes a bag filter membrane attached with stitch holes that create tiny holes or pores in the bag filter membrane to allow a leak path for free-flowing particles. Each bag may be characterized based on the size of the pores that may allow specific size particles to flow through or be trapped, known as pore diameter. An example of a commercially available filter bag may include GORE filter bags. In an embodiment, a bag filter utilized as at least a first filter 132 may have a pore diameter ranging from about 0.5 to about 12 micrometers. In an embodiment, selecting at least a first filter 132 may be performed respect to one or more variables such as the quantity of solution to be filtered and/or extracted, a degree of turbidity of the solution, or the like. Degree of turbidity may be determined, without limitation, using light sensors, where a degree of occlusion or loss of light from a light source may be used to determine a quantity and/or particle size of solid particles in suspension; in an embodiment, where degree of turbidity is above a certain amount, an additional filter stage to remove solid particles may be added, such as an initial filtration to be performed prior to filtration with ceramic filters as described below. Such determinations may be performed using a control circuit, which may contain any elements suitable for use as a control circuit in temperature regulator 208; control circuit may be combined with any control circuit as described in this disclosure. For instance, and without limitation, control circuit may display instructions to a user to perform an additional filtration step or may automatically direct solution via a pipeline or other conveyor to first filter 132 and/or one or more additional filters prior to routing to a ceramic filter as described in further detail below.

With continued reference to FIG. 1, separation of phycocyanin from solution may include separation using a centrifuge 136, defined herein as a device that rotates an object, such as a reservoir containing solution, around an axis, imposing an outward radial force on the object. The radial force separates components of a heterogenous mixture by density, which for instance may cause denser solids to migrate radially outward. Centrifuge 136 may include, without limitation, a filtration centrifuge 136, also known as a screen centrifuge 136, in which an outward wall of a drum or rotor is perforated and/or is or contains a filter, permitting liquids and/or particles smaller than a certain particle size, depending on filter pore size, to pass through while retaining solid material; filter may include any filter as described above. Removal of solid material may be performed in various ways. Filtration centrifuge 136 may include without limitation a screen and/or scroll centrifuge 136, a pusher centrifuge 136, a peeler centrifuge 136, an inverting filter centrifuge 136, a sliding discharge centrifuge 136, and/or a pendulum centrifuge 136. Alternatively or additionally centrifuge 136 may include a sedimentation centrifuge 136, in which a drum and/or rotor has a solid wall against which solid materials may precipitate, and may include without limitation a pendulum centrifuge 136, a separator centrifuge 136 including without limitation a continuous liquid centrifuge 136, a solid bowl centrifuge 136, or a conical plate centrifuge 136, a tubular centrifuge 136, and/or a decanter centrifuge 136. In an embodiment, at the end of step 120 separation of the phycocyanin from the solution, the phycocyanin may still be contained within the solution but may be physically separated inside of the solution. For example, after the biological substance in the solution has been put through a centrifuge 136, a test tube may contain the phycocyanin on the bottom of the test tube with the water on the top.

Continuing to refer to FIG. 1, before, during, or after separation of phycocyanin from solution, sterilization may occur. Sterilization may include a process that eliminates, removes, kills, or deactivates biological agents that may be present in a product, solution, compound or other object or mixture. Biological agents may include fungi, bacteria, viruses, microorganism, spore forms, prions, and/or unicellular eukaryotic organisms. Time and temperature that may be needed to sterilize an article from biological agents may be calculated by bioindicators. Bioindicators may be placed in sterilizers to confirm certain biological agents have been eliminated. Sterilization may be performed by dry heat. Dry heat may destroy biological agents by exposing biological agents to lethal temperatures. Longer exposure to lethal temperatures may cause the number of microorganisms that may be killed to increase. Dry heat may be set at temperatures in an over for example at 160 Celsius for two hours. Sterilization may also be performed by steamed heat such as with the use of an autoclave 140. An autoclave 140 may include machinery that may use steam heat at temperatures between 120-149 Celsius under pressure. An autoclave 140 may destroy biological agents by placing an article to be sterilized in a chamber and heating the article by injected steam until the article reaches a specific temperature. The chamber may have all of the air removed and the article may be kept in the chamber for a set period of time. For example, phycocyanin extract may be kept in the chamber for 3-15 minutes at 125 Celsius. Sterilization may also be performed by moist heat which may eradiate biological agents by denaturation of macromolecules found in biological agents such as proteins.

Still referring to FIG. 1, sterilization may alternatively or additionally be performed by a ceramic membrane filter and/or sterilizer. Ceramic membranes are a type of artificial membranes made from inorganic materials (such as alumina, titania, zirconia oxides, silicon carbide or some glassy materials). Ceramic membranes may have high durability, may have high resistance to aggressive media such as acids, strong solvents, and the like, and may be reused repeatedly for extended periods of time before replacement is needed, when compared with polymeric membranes and other filter designs. Ceramic membranes may have highly regular pore sizes, permitting selection of membranes to exclude solids in suspension by size; this may enable use of ceramic membranes to purify water by excluding all pathogens in water-treatment facilities, and/or to sterilize any suspension and/or solution, including a solution as described above from which phycocyanin is being extracted.

Figure 4:
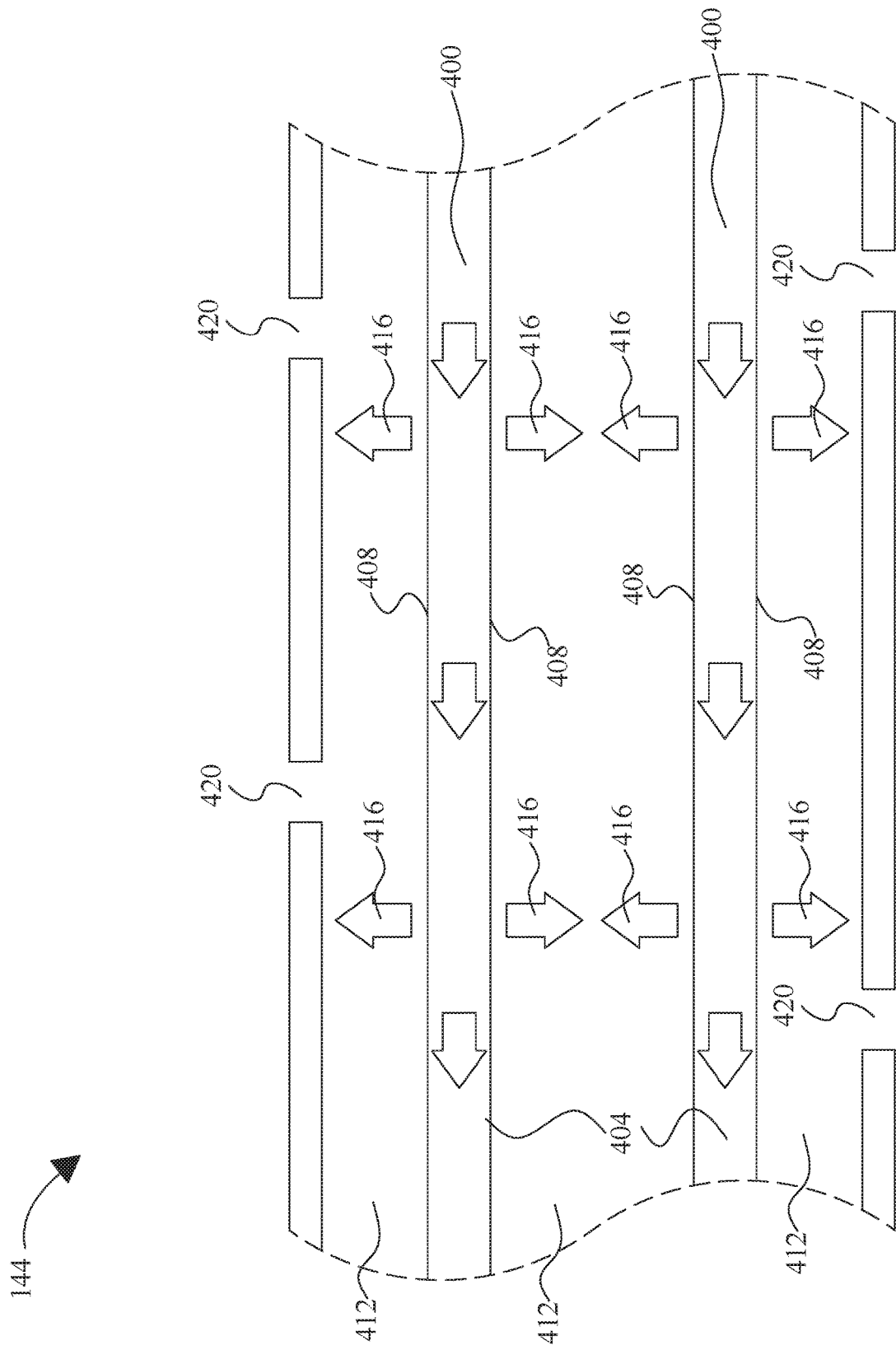
FIG. 4 is a schematic diagram illustrating an exemplary embodiment of a ceramic filter.

Referring now to FIG. 4, a schematic cross-sectional view of a ceramic filter 144 is provided for illustrative purposes. In an embodiment, unfiltered solution 400 may pass through one or more filter tubes 404 having walls 408 made up of ceramic filter 144 of a given pore size; walls 408 may include multiple concentric filters, for instance arranged in an outward radial sequence of decreasing pore sizes to filter out progressively smaller particles and/or organisms. As unfiltered solution 400 may pass through filter tubes 404, some the solution, in the form of filtrate 416 with particles excluded by walls 408, passes into filter interior 142; this filtrate 416 may be sterilized of any organisms having minimal sizes larger than the minimal pore size of walls 408. Filtrate 416 may exit filter interior 142 by one or more ports 420, where it may be passed into a new container; new container may include, without limitation, a container that is sterile and/or closed to prevent contamination. In a parallel-flow configuration as shown in FIG. 4, solution may be repeatedly passed through tubes until a desired proportion of phycocyanin-bearing fluid has been filtered out in sterilized form. Although a parallel-flow configuration is depicted, various other configurations may be used, including dead-end and/or flat sheet membranes.

Still referring to FIG. 4, ceramic membranes may have any asymmetrical structure and be composed of different porosity levels. Ceramic membranes may be formed in asymmetric, multi-channel elements. Elements may be grouped together in housings that can withstand high temperature extremes, acidity or alkalinity extremes, and/or high operating pressures. In an embodiment, ceramic membranes may exist in a variety of pore sizes from 1000 Daltons to 5 millimeters. In an embodiment, a ceramic membrane having a pore size of about 0.1 micrometers may be utilized for sterilization. A ceramic membrane may be composed of different metals including but not limited to aluminum, silicon, titanium, and/or zirconium. Ceramic membranes may sterilize an article from biological agents by filtering out biological agents from the filtered product. In an embodiment, a ceramic membrane may operate in a cross-filtration flow mode. A feed stream may flow parallel to the membrane filtration surface and generate two outgoing streams. A fraction of feed may separate out as a purified liquid passing through the membrane. The remaining fraction of feed may contain particles rejected by the membrane. Separation of the feed may be driven by a difference in pressure across the membrane. In an embodiment, this may be achieved by reverse osmosis. A parallel flow of a feed stream combined with the boundary layer turbulence created by the crossflow velocity continually sweeps away particles and other material that would otherwise build up on the membrane surface. Ceramic membranes may exist in different shapes such as round and hexagonal and may exist with various channel diameters. Any step in sterilization by any means as described above may be performed using a control circuit, which may contain any elements suitable for use as a control circuit in temperature regulator 208; control circuit may be combined with any control circuit as described in this disclosure.

Referring again to FIG. 1, process 100 may include drying extracted and/or sterilized phycocyanin to remove solution elements such as water phycocyanin may still be found. Through drying process the phycocyanin may be transformed into a powder form. Drying may be performed in a dryer 148, which may dry phycocyanin by any one of various different mechanisms. Drying may be achieved by applying hot air. Hot air may increase the drying force for heat transfer and may accelerate drying. It may also reduce air humidity, further increasing the drying process. Spray drying is a method of direct drying in which a dry powder is formed from a liquid by rapidly drying the liquid with a hot gas. A spray dryer 148 may take a liquid and separate the dissolved solute, here phycocyanin, as a solid by vaporizing the liquid solvent that the phycocyanin may still be found in. The dry powder may be collected in a drum or cyclone. The liquid input stream may be sprayed through a nozzle into a hot vapor stream where it is then vaporized. Solids may form as moisture leaves the droplets. A nozzle may make the droplets as small as possible to maximize the heat transfer and the rate of vaporization. In an embodiment, droplet size may range from 10 to 500 micrometers. Nozzles may include both high pressure single fluid nozzles and/or two-fluid nozzles. Spray dryers 148 may be single effect whereby there is a single source of drying in the spray dryer 148. Spray dryers 148 may be multiple effect whereby drying of the liquid occurs in more than one stage. Drying may also be performed by indirect or contact drying such as by heating an article through a hot wall such as drum drying and/or vacuum drying. Drying may also occur through supercritical drying whereby stream is applied to products containing water. Drying may also occur through natural air drying whereby materials may be dried with unheated forced air by taking utilizing its natural drying potential. Drying may also be performed by freeze drying methods whereby the liquid containing the phycocyanin is frozen prior to drying whereby it is then sublimed or passed to the powdered stage below the melting point of the solution, here the water. By the end of the drying process, phycocyanin may be ready to be collected as a dry powder.

Still referring to FIG. 1, one or more mechanisms (not shown) may be employed to pass liquid suspension, solution, filtrate, or other stages in process 100 between components, receptacles, devices, or the like that are performing steps of process 100 as described herein. Such mechanisms may include tubes or other open or closed conduits for conveyance of liquids from one place to another; movement of liquid may be gravity-assisted or driven by one or more mechanisms such as pumps, including without limitation peristaltic pumps or the like. Mechanisms may include conveyors such as conveyor screws, conveyor belts, or any other devices, conduits or the like for transport of solid, liquid, and/or slurry materials from one receptacle to another. In an embodiment, any receptacle including mixing vat 112, container 200, interior chamber, or the like may identical and/or shared, or may be distinct from one another. For instance, interior chamber of freezing apparatus 116 may also act as mixing vat 112; mixing vat 112 may alternatively or additionally function as cultivator 108, which may, in an exemplary embodiment, be a combined cultivator 108, mixing vat 112, and freezing apparatus 116. Mixing vat 112 may be placed within outer chamber 304 of freezing apparatus 116 for freezing steps and/or removed for thawing, mixing, and/or chemical introduction steps. Each conveyance and/or transfer step may be performed and/or activated manually; alternatively or additionally, each conveyance and/or transfer step may be performed automatically, for instance using a control circuit, which may contain any elements suitable for use as a control circuit in temperature regulator 208; control circuit may be combined with any control circuit as described in this disclosure.

Figure 5:
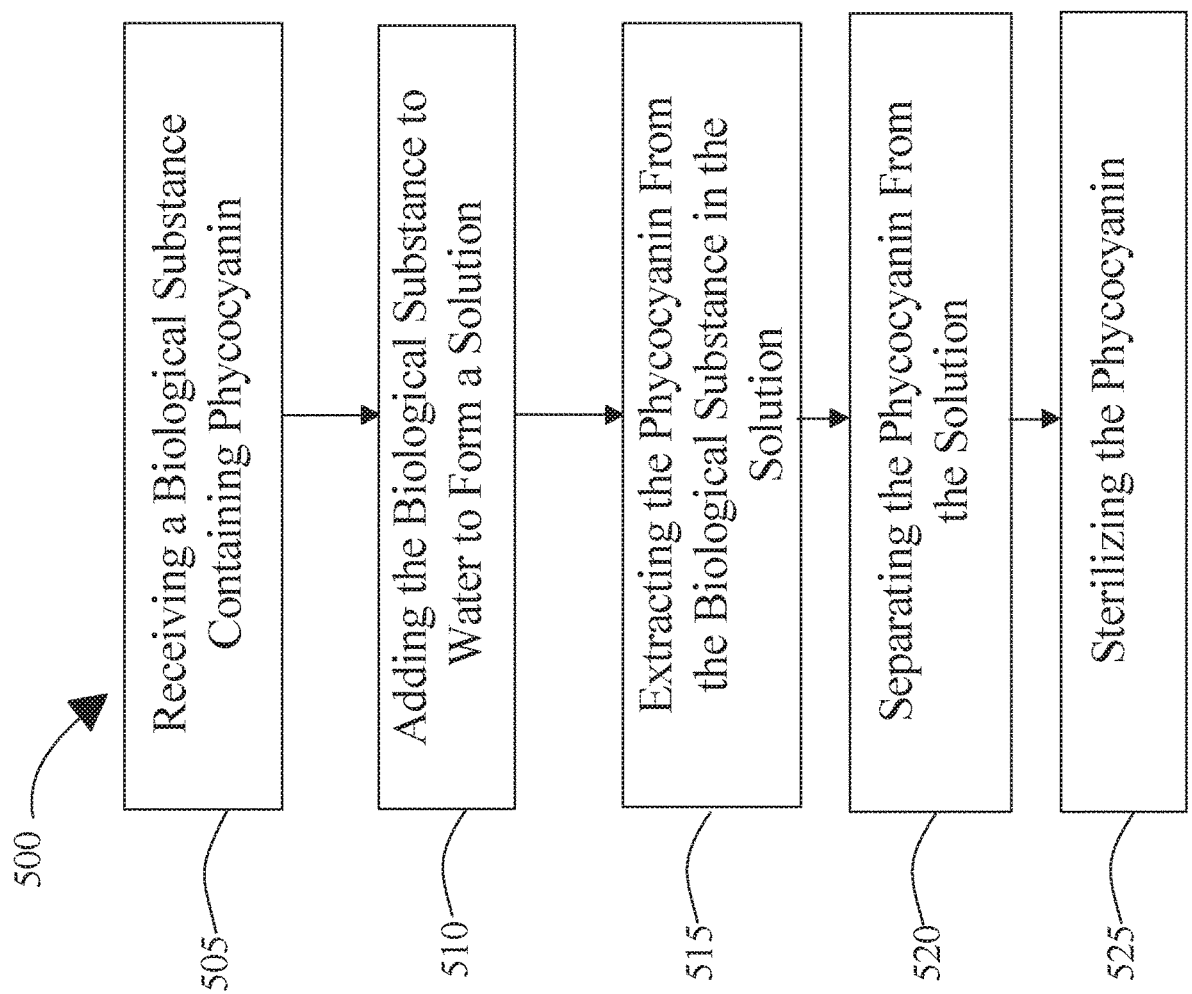
FIG. 5 is a flow diagram illustrating a method of synthesizing phycocyanin using a powdered biological substance.

Referring now to FIG. 5, an exemplary embodiment of a method 500 for synthesizing phycocyanin using a biological substance is illustrated. At step 505, a biological substance containing phycocyanin is received. This may be accomplished, without limitation, according to any process described above in reference to FIG. 1 for receipt of biological substance. As a non-limiting example, biological substance may be cultivated and/or grown in cultivator 108 as described above and/or received alive or dead in powdered or other form. Biological substance may include cell membranes containing phycocyanin and extracting the phycocyanin further comprises fracturing the cell membranes containing phycocyanin.

With continued reference to FIG. 5, at step 510 biological substance is added to water to form a solution. This may be performed in mixing vat 112 and/or cultivator 108; this step may be included in a step of cultivation and/or reception of biological substance, by adding powdered biological substance, a slurry, cake, paste, or any other form of biological substance to water and/or an aqueous solution.

Continuing to refer to FIG. 5, at step 115 phycocyanin is extracted from a cell membrane of the biological substance in the solution. Extracting may include freezing and thawing the solution at least once, for instance as described above in reference to FIGS. 1-4. Freezing may, for instance and without limitations, adding the solution to a container of ice 308. Container of ice 308 may be kept at a target temperature and/or temperature range, including without limitation a temperature below about 0 degrees Celsius, a temperature below about −10 degrees Celsius, a temperature between about −10 and about −30 Celsius, and/or a temperature within some tolerance number of degrees, such as without limitation 1 degree, 5 degrees, or the like about a target temperature, which may include without limitation any temperature described above and/or any temperature falling within ranges as described above. Each target temperature may be maintained, without limitation, using a control circuit, which may contain any elements suitable for use as a control circuit in temperature regulator 208; control circuit may be combined with any control circuit as described in this disclosure. Solution may be repeatedly stirred during freezing; this may be coordinated, without limitation, using a control circuit, which may contain any elements suitable for use as a control circuit in temperature regulator 208; control circuit may be combined with any control circuit as described in this disclosure.

With continued reference to FIG. 5, extracting may include addition of one or more chemical reagents 124 to solution. For instance, and without limitation, extracting may include adding a first chemical reagent to the solution. A first chemical reagent added to the solution may include a salt. A first chemical reagent may be added to the solution at a mass ratio whereby when the mass ratio of powdered biological substance and water is 1 part powdered biological substance: 15 parts water then a first chemical reagent may be added as 0.7 parts first chemical reagent: 1 part powdered biological substance: 15 parts water (0.7:1:15). A first chemical reagent may be added to the solution at a mass ratio whereby when the mass ratio of powdered biological substance and water is 1 part powdered biological substance:8 parts water then a first chemical reagent may be added as 0.7 parts first chemical reagent: 1 part powdered biological substance: 8 parts water (0.7:1:8). For example, using the mass ratio of 0.7 parts first chemical reagent to 1 part powdered biological substance to 8 parts water may equate to 35 kilograms first chemical reagent to 50 kilograms powdered biological substance to 400 kilograms water.

In an embodiment, adding a first chemical reagent to the solution may include adding the first chemical reagent in a quantity having a ratio by mass of between 1 part:25 parts and 1part:15 parts when the mass ratio of powdered biological substance and water is 1 part:15 parts and 1 part:8 parts respectively. First chemical reagent may be alkaline or base; an alkaline or base may be a substance having a PH greater than 7, which may accept protons (such as positive hydrogen ions) from proton donors when in solution.

Continuing to refer to FIG. 5, extracting may include adding a second chemical reagent to the solution. A second chemical reagent added to the solution may include a chloride-containing compound, such as without limitation sodium hypochlorite. A second chemical reagent may also include sodium bicarbonate, citric acid and/or tartaric acid. A second chemical reagent may be added to the solution at a mass ratio whereby when the mass ratio of powdered biological substance and water is 1 part:15 parts then a second chemical reagent may be added as 0.00087 parts second chemical reagent: 1 part powdered biological substance: 15 parts water (0.00087:1:15). A second chemical reagent may be added to the solution at a mass ratio whereby when the mass ratio of powdered biological substance and water is 1 part:8 parts then a second chemical reagent may be added as 0.00087 parts second chemical reagent: 1 part powdered biological substance: 8 parts water (0.00087:1:8). For example, using the mass ratio of 0.00087 parts second reagent to 1 part powdered biological substance to 8 parts water may equate to 0.04372 kilograms second chemical reagent to 50 kilograms powdered biological substance to 400 kilograms water. In an embodiment, 5-40 ml of a second chemical reagent may be added to the solution for every 50 kg of powdered biological substance that may be in solution. For example, when 50 kg of powdered biological substance is added to solution, 5-40 ml of a second chemical reagent may be added to the solution. When 100 kg of powdered biological substance is added to solution, 10-80 ml of a second chemical reagent may be added to the solution. Adding the second chemical reagent may include adding the second chemical reagent in a quantity having a ratio by mass to the powdered biological substance and water of between 1:20,000 and 1:10,000 when the mass ratio of powdered biological substance to water is between 1:15 and 1:8 respectively. In an embodiment, a second chemical reagent may not be added sequentially after a first chemical reagent.

For example, a first chemical reagent may not be added, and only a second chemical reagent may be added. In an embodiment, a first chemical reagent may be added after a second chemical reagent; first chemical reagent and second chemical reagent may be added simultaneously, alternately, or in any other sequence and/or combination. In an embodiment, solution containing second chemical reagent, with or without first chemical reagent, may be stirred or spun using any suitable means for stirring or spinning solution containing first chemical reagent as described above. Spinning and/or stirring of solution containing second chemical reagent may be performed for a first period of time; spinning and/or stirring may be done for a time period of two hours after a second chemical reagent has been added to the solution, as a non-limiting example. In an embodiment, a second reagent may be added after a first reagent in a sequence whereby after a second reagent has been added to a solution containing a first reagent and spun for 2-8 hours, spinning is then stopped for 3-12 hours, then a third reagent is added, the resulting solution is then stirred for 6-24 hours, and then a fourth reagent is added. In an embodiment, spinning of the solution containing the second chemical reagent may be ceased, and the solution may be allowed to rest for a second period of time; for instance, and without limitation, solution may be allowed to rest without stirring for a time period of at least six hours. Spinning may be performed automatically such as for example with the use of magnetic spinner. A magnetic spinner may include a device that employs a rotating magnetic field to cause a spinning bar immersed in the solution to spin, thus spinning it.

With continued reference to FIG. 5, extracting may include adding a third chemical reagent to the solution. A third chemical reagent added to the solution may include an acid. An acid may include a substance with a pH of less than 7 and which may donate protons and react with metals such as calcium for example to form salts. For example, a third chemical reagent may include tartaric acid, acetic acid, and/or oxalic acid. A third chemical reagent may also include magnesium sulfate, disodium hydrogen phosphate, and/or sodium nitrate. A third chemical reagent may be added to the solution at a mass ratio whereby when the mass ratio of a powdered biological substance and water is 1 part:15 parts then a third chemical reagent may be added as 0.48 parts third chemical reagent: 1 part powdered biological substance: 15 parts water (0.48:1:15). A third chemical reagent may be added to the solution at a mass ratio whereby when the mass ratio of a powdered biological substance and water is 1 part:8 parts then a third chemical reagent may be added as 0.48 parts third chemical reagent: 1 part powdered biological substance: 8 parts water (0.48:1:8). For example, using the mass ratio of 0.48 parts third reagent to 1 part powdered biological substance to 8 parts water may equate to 24 kilograms third chemical reagent to 50 kilograms powdered biological substance to 400 kilograms water. A third chemical reagent may be added to the solution between 1:35 parts when a powdered biological substance is 15 parts and 1 part water. In an embodiment, a third chemical reagent may not be added sequentially after a first chemical reagent and/or a second chemical reagent, and/or may not be added at all. For example, a first chemical reagent and a second chemical reagent may not be added, and only a third chemical reagent may be added. Alternatively or additionally, a first chemical reagent and a third chemical reagent may be added to the solution. Alternatively or additionally a second chemical reagent may be added followed by a third chemical reagent followed by a second chemical reagent. In an embodiment, a first chemical reagent may be added after a third chemical reagent. In an embodiment, a fourth chemical reagent may be added to the solution. A fourth chemical reagent may include any of the reagents described above, and/or a fourth chemical reagent may be a new compound. In an embodiment a fourth chemical reagent may be optional.

Still referring to FIG. 5, in an embodiment, first, second, third, and/or fourth reagents may react with one another to remove at least one of first, second, third, and/or fourth reagent from solution. For example, and without limitation, one reagent of first, second, third, and/or fourth reagents may have an acidic PH while another has an alkaline PH; as a result, alkaline and acid reagents may react, converting the combined chemicals to a solid precipitate and/or gas, which may then be removed by ventilation, centrifuge 136, or the like. In an embodiment, chemical reagents 124 are added in relative quantities sufficient to cause one or all of the chemical agents to be removed entirely from solution, and/or to be removed to a concentration below some desired level. Persons skilled in the art, upon reviewing the entirety of this disclosure, will be aware of various ways in which reagents may be combined to remove one or all such reagents to a desired concentration or tolerance.

With continued reference to FIG. 5, in an embodiment a chemical reagent such as a lysate may be added as a first, second, third, and/or fourth reagent. Addition of first, second, third, and/or fourth reagent may include determining a concentration of the biological substance in the solution, which may be accomplished according to any process described above, and selecting a quantity of at least one of the first chemical, the second chemical, and the third chemical to add to the solution as a function of the concentration of biological substance in the solution.

Continuing to refer to FIG. 5, at step 520 phycocyanin is separated from the solution. This may be accomplished according to any process and/or process steps described above. For instance, and without limitation, separating the phycocyanin from the solution may include adding the solution to a centrifugal separator; in an embodiment, a centrifuge 136 used to separate phycocyanin may accelerate at rotation speeds of 6000-7000 rpm. Separating the phycocyanin may include filtering the solution through a first filter 132 to form a filtrate. Separating may include concentrating the solution; for instance solution may be concentrated to a molecular weight between 3000 and 5000 Daltons.

With continued refence to FIG. 5, at step 525 the separated phycocyanin is sterilized; this may be accomplished according to any process and/or process steps described above. For instance, and without limitation sterilization may be performed using heat, for instance by means of an autoclave 140. Alternatively or additionally, sterilizing separated phycocyanin may include sterilizing utilizing a ceramic membrane sterilizer, for instance as described above. Ceramic membrane may include a pore size of 0.1 micrometer. Separated phycocyanin may be dried, using any process or process steps described above.

With continued reference to FIG. 5, and by way of an illustrative example, phycocyanin may be extracted and produced by the following preparation. *Spirulina* powder weighing 50 kilograms may be dissolved in 400 kilograms of water. The solution containing the powdered *spirulina* and water may then be placed in a freezer at −18 Celsius. Freezing and thawing may be performed a series of 4 times. A first reagent consisting of 35 kilograms of sodium chloride may be added to the solution, followed by a second reagent consisting of 18 kilograms of tartaric acid, followed by a third chemical reagent consisting of 40 ml of sodium hypochlorite. The three chemical reagents 124 may be spun for 2 hours, whereby spinning is then stopped for 6 hours. A fourth chemical reagent consisting of 8 kilograms magnesium sulfate was added and then stirred for 16 hours. The resulting solution may then be filtered with a plate and frame filter, followed by a bag filter with a diameter of 10 micrometers. The solution may then be spun in a centrifuge 136 rotating at a speed of 6000-7000 rotations per minute. The resulting solution may then be concentrated to a molecular weight of 5000 Daltons and then sterilized with a ceramic membrane sterilizer. The resulting product may be dried with heat and a powder may be collected.

With continued reference to FIG. 5, in an embodiment, phycocyanin may be extracted and produced by the following preparation. *Chlorella* powder weighing 50 kilograms may be dissolved in 500 kilograms of water. The solution containing the powdered *chlorella* and water may then be placed in a freezer at −18 Celsius. Freezing and thawing may be performed a series of 5 times. A first reagent consisting of 25 kilograms of copper sulfate solution may be added to the solution, followed by a second reagent consisting of 10 kilograms of sodium bicarbonate, followed by a third chemical reagent consisting of 10 ml of sodium hypochlorite. The resulting solution may then be spun for 3 hours, and then spinning was stopped for 8 hours. A fourth chemical reagent consisting of 15 kilograms of disodium hydrogen phosphate may be added, and then stirred for 12 hours. The resulting solution may be filtered with a plate and frame filter, followed by a bag filter with a diameter of 3 micrometers. The solution may then be spun in a centrifuge 136 rotating at a speed of 6000-7000 rotations per minute. The resulting solution may be concentrated to a molecular weight of 3000 Daltons and then sterilized with a ceramic membrane sterilizer. The resulting product may be air dried and the resulting powder collected.

With continued reference to FIG. 5, in an embodiment, phycocyanin may be extracted and produced by the following preparation. Cyanobacterial algae blooms powder weighing 50 kilograms may be dissolved in 600 kilograms of water. The solution containing the powdered cyanobacterial algae blooms and water may then be placed in a freezer at −18 Celsius. Freezing and thawing may be performed a series of 6 times. A first reagent consisting of 45 kilograms of potassium chloride solution may be added to the solution, followed by a second reagent consisting of 4 kilograms of citric acid, followed by a third chemical reagent consisting of 25 ml of acetate. The resulting solution may be spun for 2 hours, and then spinning may be stopped for 6 hours. A fourth chemical reagent consisting of 32 kilograms of disodium hydrogen may be added, and then stirred for 16 hours. The resulting solution may be filtered with a plate and frame filter, followed by a bag filter with a diameter of 7 micrometers. The solution may then be spun in a centrifuge 136 rotating at a speed of 6000-7000 rotations per minute. The resulting solution may then be concentrated to a molecular weight of 5000 Daltons and then sterilized with a ceramic membrane sterilizer. The resulting product may then be air dried and the resulting powder collected.

With continued reference to FIG. 5, in an embodiment, phycocyanin may be extracted and produced by the following preparation: *Nannochloropsis* powder weighing 50 kilograms may be dissolved in 700 kilograms of water. The solution containing the powdered *nannochloropsis* and water may then be placed in a freezer at −18 Celsius. Freezing and thawing may be performed a series of 4 times. A first reagent consisting of 10 kilograms of calcium chloride solution may be added to the solution, followed by a second reagent consisting of 13 kilograms of citric acid, followed by a third chemical reagent consisting of 24 ml of oxalic acid. The resulting solution may then be spun for 2 hours, and then spinning may be stopped for 6 hours. A fourth chemical reagent consisting of 21 kilograms of sodium nitrate may be added, and then stirred for 16 hours. The resulting solution may then be filtered with a plate and frame filter, followed by a bag filter with a diameter of 10 micrometers. The solution may then be spun in a centrifuge 136 rotating at a speed of 6000-7000 rotations per minute. The resulting solution may then be concentrated to a molecular weight of 5000 Daltons and then sterilized with a ceramic membrane sterilizer. The resulting product may be air dried and the resulting powder collected.

Still referring to FIG. 5, the examples provided above are for the purposes of illustration only, as indications of processes that may be followed in exemplary embodiments of the above-disclosed method; the examples should not be construed as limiting in any way. Persons skilled in the art, upon reading the entirety of this disclosure, will be aware of various alternatives that may be employed to practice methods within the scope of this disclosure.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
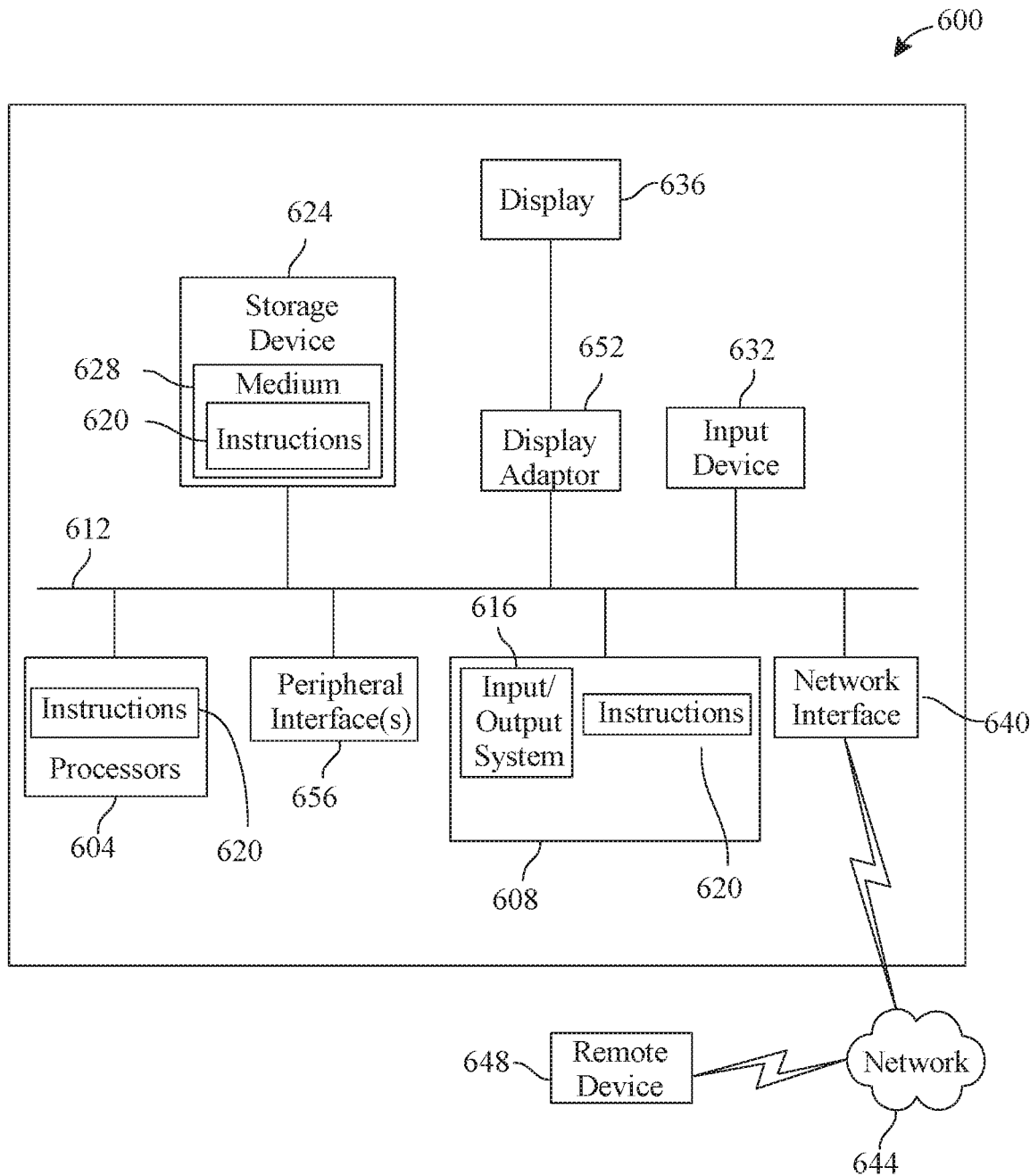
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods as described in this disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A purification method comprising:
   receiving a biological substance containing phycocyanin;
   adding the biological substance containing phycocyanin to water to form a solution;
   extracting phycocyanin from the biological substance containing phycocyanin in the solution;
   separating the phycocyanin from the solution to form a separated phycocyanin;
   sterilizing the separated phycocyanin, wherein sterilizing the phycocyanin further comprises sterilizing the separated phycocyanin using a ceramic membrane; and
   drying the separated phycocyanin.

2. The method of claim 1, wherein receiving a biological substance further comprises cultivating the biological substance.

3. The method of claim 1, wherein the biological substance includes cell membranes containing phycocyanin, and extracting the phycocyanin further comprises fracturing the cell membranes containing phycocyanin.

4. The method of claim 1, wherein extracting further comprises freezing and thawing the solution at least once.

5. The method of claim 4, wherein freezing further comprises adding the solution to a container of ice.

6. The method of claim 5, wherein the container of ice is kept at a temperature between about −10 degrees Celsius and about −30 degrees Celsius.

7. The method of claim 6, wherein the solution is repeatedly stirred during freezing.

8. The method of claim 1, wherein extracting further comprises adding a first chemical reagent to the solution.

9. The method of claim 8, wherein the first chemical reagent is a salt.

10. The method of claim 8, wherein extracting further comprises adding a second chemical reagent to the solution.

11. The method of claim 10, wherein the second chemical reagent is a chloride-containing compound.

12. The method of claim 8 further comprising stirring the second chemical reagent solution for two hours.

13. The method of claim 12 further comprising ceasing stirring of the solution containing the second chemical reagent and allowing to sit for at least 6 hours.

14. The method of claim 12, wherein extracting further comprises adding a third chemical reagent.

15. The method of claim 14 further comprising:
    determining a concentration of the biological substance in the solution; and
    selecting a quantity of at least one of the first chemical, the second chemical, and the third chemical to add to the solution as a function of the concentration of biological substance in the solution.

16. The method of claim 1, wherein separating the phycocyanin further comprises filtering the solution through a first filter.

17. The method of claim 1, wherein the ceramic membrane has a pore size of 0.1 micrometer.

18. The method of claim 1, wherein the separated phycocyanin comprises an ammonium salt by mass.

* * * * *